United States Patent
Chevillon et al.

(10) Patent No.: US 6,511,506 B2
(45) Date of Patent: *Jan. 28, 2003

(54) MEDICAL SET FOR INTERVENTION ON AN ANATOMICAL DUCT, SEALING RING PERTAINING TO SAID SET AND USE OF SAID RING

(75) Inventors: Gérard Chevillon, Montrouge (FR); Guy Nadal, Poitiers (FR); Samy Anidjar, Paris (FR)

(73) Assignee: B. Braun Celsa, Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/870,520

(22) Filed: Jun. 1, 2001

(65) Prior Publication Data

US 2002/0022891 A1 Feb. 21, 2002

Related U.S. Application Data

(62) Division of application No. 09/308,934, filed on Aug. 4, 1999, now abandoned.

(30) Foreign Application Priority Data

Oct. 1, 1997 (FR) .............................. 97 12231
May 12, 1998 (FR) .............................. 98 05946
Jun. 15, 1998 (FR) .............................. 98 07527

(51) Int. Cl.$^7$ .................................................. A61F 2/06
(52) U.S. Cl. .................... 623/1.36; 623/903; 606/151
(58) Field of Search .............................. 623/1.13, 1.14, 623/1.23, 1.36, 903; 606/151, 153; 423/1.13, 1.14, 1.27, 1.36

(56) References Cited

U.S. PATENT DOCUMENTS

| | | | | |
|---|---|---|---|---|
| 3,726,279 A | * | 4/1973 | Barefoot et al. | 606/151 |
| 4,190,909 A | * | 3/1980 | Ablaza | 623/1.32 |
| 5,041,126 A | * | 8/1991 | Gianturco | 623/1.15 |
| 5,123,917 A | * | 6/1992 | Lee | 623/1.13 X |
| 5,527,355 A | * | 6/1996 | Ahn | 623/1.36 |
| 5,665,117 A | * | 9/1997 | Rhodes | 606/194 X |
| 5,707,378 A | * | 1/1998 | Ahn et al. | 606/139 |
| 6,063,112 A | * | 5/2000 | Srgo | 623/1.12 |
| 6,248,116 B1 | * | 6/2001 | Chevillon et al. | 606/139 |

FOREIGN PATENT DOCUMENTS

| | | |
|---|---|---|
| EP | 0579523 | 1/1994 |
| WO | 9015582 | 12/1990 |
| WO | 9607371 | 3/1996 |
| WO | 9719653 | 6/1997 |

* cited by examiner

Primary Examiner—Paul B. Prebilic
Assistant Examiner—Brian Pellegrino
(74) Attorney, Agent, or Firm—Rothwell, Figg, Ernst & Manbeck

(57) ABSTRACT

A method for implanting a medical set in a human blood vessel, the medical set comprising a prosthesis adapted to be introduced in the vessel, the prosthesis having a first end and a second end, and being adapted to be disposed against an inner wall of the vessel at least at one of the ends, the prosthesis comprising a tubular sleeve and a strap adapted to be disposed against the vessel at a location adjacent one of the ends of the tubular sleeve, the strap having a hemostatic covering for reducing any blood leakage at the location of the strap.

8 Claims, 4 Drawing Sheets

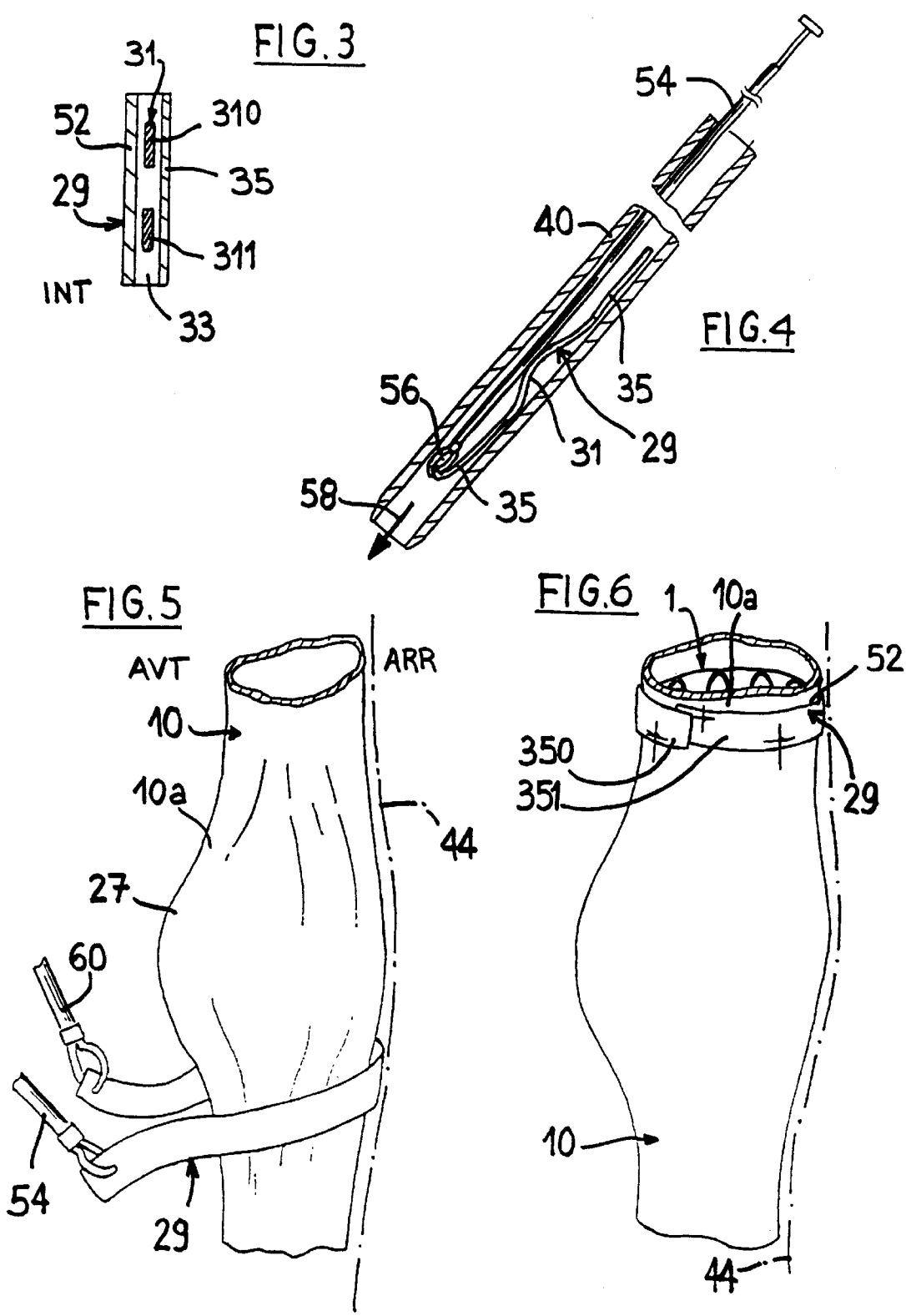

MEDICAL SET FOR INTERVENTION ON AN ANATOMICAL DUCT, SEALING RING PERTAINING TO SAID SET AND USE OF SAID RING

CROSS-REFERENCE TO RELATED APPLICATION

This application is a divisional of application Ser. No. 09/308,934, filed Aug. 4, 1999 now abandoned.

BACKGROUND OF THE INVENTION

1. Field of the Invention

The field of the invention relates to bifurcated or rectilinear tubular prostheses designed to be implanted in a human duct, or an animal duct, for maintaining or recovering a path therein.

2. Description of the Related Art

Especially, the invention applies to such a prosthesis to be disposed at the location of a vascular aneurism (in particular of the aorta) for isolating said aneurism, while creating there a substitute of the wall of the vessel, so that the blood can still circulate.

Various prostheses (or implants) designed to be disposed at the location of an aneurism are known, those prostheses being either self-expandable (viz. expandable without inner radial strength, through self elasticity or shape memory) or expandable by means of a complementary means creating an enlarging radial internal force (such as a balloon). Those prostheses generally comprise a metallic structure comprising at least one stent (or enlarger) adapted to be supported on the vessel wall, at least on one side of the aneurism, at a location called upper neck, by creating a force for enlarging the prosthesis towards the vessel wall.

The upper neck (or upstream neck) means the portion of the vessel wall located above the aneurism and lower neck means the portion of the vessel wall located just downstream the aneurism (relative to the blood flow).

Those prostheses are typically covered with a covering sheath which is disposed inside or outside the metallic structure and is (or becomes) impervious. They can be implanted in the vessel to be treated, for example through a transcutaneous, endoluminal way (in particular by the method called of SELDINGER) before self-expanding or before being expanded in said vessel and then fixed to the wall. This type of prostheses is in particular described in FR-A-2 732 404, U.S. Pat. Nos. 5,591,229, 5,330,500 or EP-A-0 696 447.

A problem is that those prostheses are generally insufficiently adapted to the implanting conditions, in particular at the upper neck of an aneurism. The shape of this neck (taken along its section, or longitudinally) is often not regular (curved, with a variable section, covered with various cellular aggregates or hollows) and very often different from one patient to another. Therefore, there is a hard adequation between the stent of the prosthesis and the wall of the duct. Furthermore, after a while, the duct tends to locally inflate under the action of the prosthesis and thus tends to be separated therefrom. Further, the prosthesis is sometimes incorrectly fixed to the duct and then risks to inopportunately move.

U.S. Pat. Nos. 5,527,355 or 5,507,378 describes a medical set designed to be implanted in an anatomical duct and comprising:

an intraluminal prosthesis comprising a structure adapted to take up a first radially constricted state, to be inserted into the duct, and a second radially unfolded state wherein the structure has a general shape of a single or bifurcated tube to rest, at least at its upper proximal end, against the wall of said duct, near the upstream zone thereof, and at least a collar adapted to be disposed around the duct, in front of the proximal end of the prosthesis, for maintaining it against the duct when the set is implanted.

SUMMARY OF THE INVENTION

Nevertheless, an object of the invention is to provide a strap, or collar, for locally lining the zone of the duct wall to be treated with a view to improving the conditions of a laparoscopic implantation (also called coelioscopy or endoscopy), thus reducing the risks of the intervention (perforating the duct, alterating the nearby organs, . . . ) and making the intervention proceedings easier (easiness for moving the strap and the fixation of the strap and the prosthesis). Tightly maintaining the prosthesis is further requested.

The solution consists in using a collar which is, for its portion to be disposed in front of the anatomical duct to be treated, structured enough to be more rigid than a strap only, such as in U.S. Pat. No. 5,527,355.

In particular, the ring or collar used as sealing tight means outside and around the duct can comprise a core having the shape of a split ring naturally curved and resilient, the core being fixed to a flexible, elongated strap which is divisible and extends beyond the perimeter of the core. Thus, implementing a structured portion as a split ring is recommended.

Then, the advantage consists in having both a splitted ring adapted to be elastically disposed around the duct and a lace or strap, in particular made of fabric, which is very convenient for fitting the diameter of the sealing tight ring to the duct one.

According to another preferred feature of the invention, the core will be covered by a protecting covering made of a self-sealing material, while the covering covers the core at least over an external surface thereof (to be fixed thereto).

A specific application relates to using this prosthesis with its collar(s) at the location of the vascular aneurism, while the collar and the prosthesis are preferably disposed at the location of the upstream and downstream aneurism necks.

Using a radially deformable collar, which is preferably resiliently deformable, gives the opportunity to use an easily implantable means adapted to naturally fit the exact shape of the duct and the prosthesis. Further, designing a naturally adaptable means, viz. adapted to be disposed around ducts having various sections and pertaining to a sole patient or various patents, is allowed.

According to a further consideration, the prosthesis may comprise, in front of the (each) collar, a (further) radially deformable strengthener disposed within the corresponding duct, and consisting of at least an element or a portion of a metallic, annular structure so located that the duct wall is interposed between said element and the collar. Thus, if the duct is an aneurism, the prosthesis will still be further pressed to the duct wall. Furthermore, maintaining the prosthesis will be improved.

Together with, or in place of, this inner ring the prosthesis can be locally lined with an annular pad to be pressed to the internal, peripheral duct wall, for improving the sealing where the duct is squeezed.

According to a further consideration, the external surface of the above-mentioned inner ring can be slightly abrasive and/or non-skid for still accurately maintaining the implant in its receiving duct.

According to another feature, the invention takes into consideration the accuracy of implantation to be obtained, together with the easiness for the practitioner to fix the collar to the prosthesis, through the duct.

Therefore, it is recommended to include a radio-opaque mark within the collar, and in particular, to provide the core (or the strengthening structure) of this ring with two radio-opaque locating strips (for example made of metal) disposed substantially parallel and separated one from the other. Those strips delimit therebetween a zone defining, for the practitioner, a preferred zone for fixing the prosthesis.

For still improving the quality of the imperviousness, substantially whatever the duct perimeters are, said perimeters being allowed to change from one patient to another, a further feature of the invention recommends that the self-sealing protecting cover extends beyond the perimeter of the core, along the extended strands of the strap.

Thus, the practitioner will typically be in position to sealingly fix his collar to the prosthesis, through the duct. If necessary, he will adjust the length of this protecting cover by cutting it, since it is made of a divisible material (silicone, for example).

Further to the above-disclosed set, the invention relates to a method for implanting a prosthesis in its reception duct, the prosthesis being unfolded in situ, so that an external surface thereof is tightly pressed to an internal duct wall, at the location of an interface zone.

Preferably:
the external covering collar will be introduced around the corresponding zone(s) of the duct, through a percutaneous way (coelioscopy, in particular),
and the prosthesis will be percutaneously and endoluminally implanted, through said duct, and will be unfolded in the duct for obtaining a sealing barrier (seal) between the external surface of the prosthesis and the inner wall of the anatomical duct.

Advantageously:
the external lining collar will be introduced in its second state(substantially flat or with a very small diameter) in an introducing catheter, as far as the immediate vicinity of the external wall of the corresponding duct,
then, the collar will be pushed out of its introducing catheter for adopting its first state (curved) around the duct,
and it will be fixed to the prosthesis (already opened in the duct) by means of the above-mentioned fixation means brought near the prosthesis through coelioscopy (or laparoscopy) and thus introduced towards the prosthesis, from outside the duct, through the wall thereof.

It is to be noted that the invention further offers means to be used for improving the implantation of the external ring around the duct.

For this aim, the medical set will comprise:
a sheath, or a trocar, for a laparoscopy, adapted for introducing the collar within the patient body, up to the vicinity of the external wall of the duct,
and pliers for maneuvering the collar, the pliers being adapted to be slid in the sheath (or the trocar) beside the collar, the splitted annular portion of which is then opened to a stressed, substantially flat deformed position.

It will also be noted that, according to one aspect of the invention, the collar can be used as a lace for moving the corresponding duct, especially if the duct is a vessel.

In such a case, the surgeon will have to staunch one or more bleeding(s) from the vessel.

Thus, another feature of the invention recommends to provide the above-mentioned collar with an hemostatic structure, layer or cover, for reducing such a bleeding where the collar is pressed to the corresponding vessel.

BRIEF DESCRIPTION OF THE DRAWINGS

The invention and the application thereof will still be more clear from the following description concerning an aneurism treatment and made with reference to the enclosed drawings in which:

FIG. 3 is a section of the ring along line III—III of FIG. 2, FIG. 4 schematically illustrates, along a partial section, a coelioscopic trocar, together with coelioscopic pliers adapted to be used for introducing a ring according to the invention, FIG. 5 relates to the ring used as a lace, and then maneuvered by two coelioscopic pliers, FIG. 6 shows the lace of FIG. 5, at the end of the intervention, tightly fixed around the vessel (presently the upper neck), in an impervious manner.

DETAILED DESCRIPTION OF THE PREFERRED EMBODIMENTS

Below, the description only refers to treating a vessel aneurism, even if other anatomical ducts may be concerned.

Figure 1:
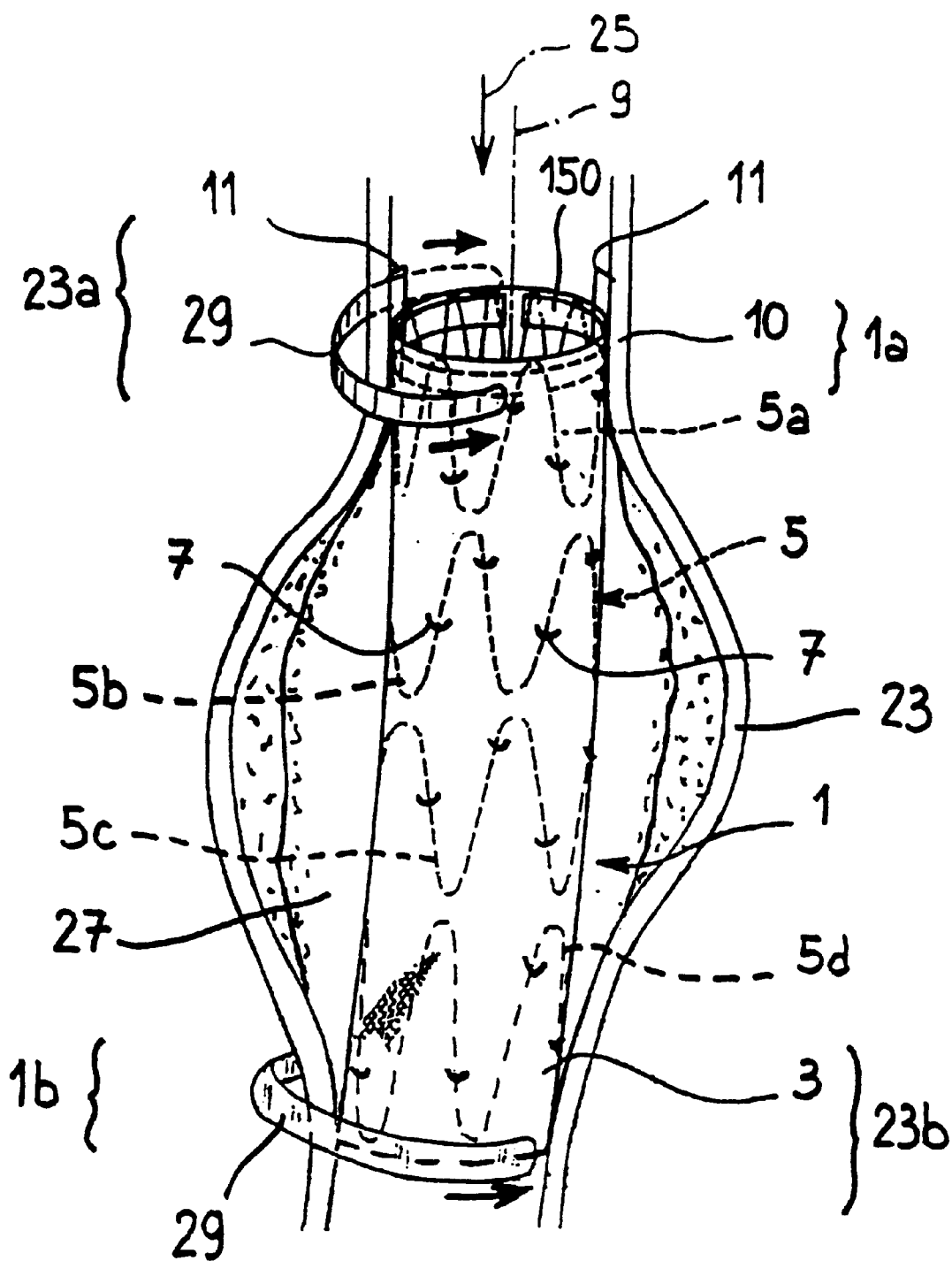
FIG. 1 is a perspective, schematic view of a vessel affected with an aneurism and enclosing an aneurism prosthesis together with two schematically illustrated sealing rings.

At first, in FIG. 1 is illustrated a conventional aneurism prosthesis, 1.

This implant comprises a usual, flexible, tubular sleeve 3, typically made of cloth (for example, Dacron, TM) and adapted for canalizing blood therethrough.

A frame consisting of a stent structure referenced as 5, provides the sleeve 3 with a mechanical strength, while being connected thereto with one or more surgical threads 7 for suture.

The structure 5 can have two states:
a first state having a restrained diameter (not illustrated) for introducing the implant within the receiving vessel (the method of SELDINGER can typically be used),
or a second state having a larger diameter (see FIG. 1) wherein the implant is at least locally substantially pressed to the internal wall of the vessel.

The stent structure 5 can consist of self-expandable stent (s) typically made of metal, such as inoxydable steel, or which are expandable by means of an inflatable balloon (not illustrated). Making the structure of a shape memory material, in particular a nickel/titanium alloy (Nitinol, TM) is also admissible.

In the example of FIG. 1, the stent structure 5 is staggered along a lot of stages, presently 5a, 5b, 5c, 5d. Each stage is made of an ondulated metallic thread (such as a zigzag) closed on itself for defining a cylindrical ring (or perforated tube) having a variable diameter.

The stages 5a and 5d are respectively located towards the upstream free end 1a, and the downstream free end 1b of the implant (in reference to the blood stream).

The structure 5 can be disposed inside or outside the sleeve 3 which is constricted or radially opened (relative to the axis 9 of the implant) according to the radial state of the structure 5.

It is to be noted that a shape other than consisting of ondulated thread(s) could be used for structure 5.

For fixing the implant 1 to the vessel 10 within which said implant is already disposed, the implant can comprise anchoring hooks, such as referenced 11, made of metal and having a tip adapted to pierce the vessel wall. In FIG. 1, they extend beyond the upstream end la and are connected to stage 5a.

Complementarily to, or instead of, such hooks, using fixing means connected to complementary sealing means but different from said hooks, is recommended.

As described in FR 97 16625, filed on Dec. 29, 1997, these means are fixing means passing through all the vessel wall 10, and/or fixed thereto from the external vessel wall, such as rivets which are different from the hooks 11 which are not designed to pass through this wall, and which are hooked from the inner side of the vessel.

Another efficient approach for fixing can consist in suturing (with one or more known thread(s) for a surgical suture) the implant to the vessel, a priori from outside the vessel, while using an extravascular, coelioscopic approach.

Whatever these transvascular fixing means can be, they are preferably disposed both at the upstream end 23a and downstream end 23b of the aneurism diagrammatically illustrated in 23 in FIG. 1, except where the prosthesis, as described in FR-A-2 748 198, the sleeve of which is free of stent at its downstream end and is there anastomosed to the facing duct wall, is used.

Those fixing means are associated to external reinforcing/sealing means 29 for preventing the blood flow (arrow 25 for the main flow) to still pass into the aneurism sac 27 (directly or through a reflux via collateral vessels) and also for preventing the necks of the vessel from inflating.

Figure 2:
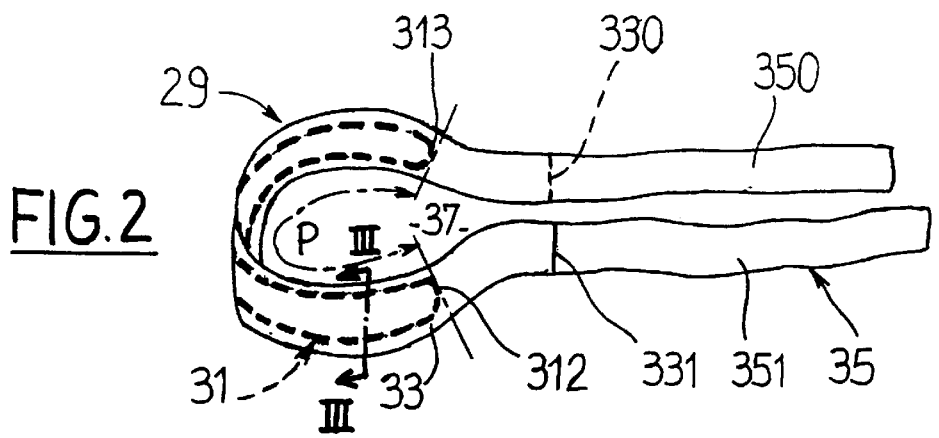
FIG. 2 is more a detailed, enlarged view of a sealing ring.

In FIG. 2, the illustrated sealing means 29 comprise a mechanically structuring core 31 having the shape of a split ring or collar (not entirely closed on itself), naturally curved and resilient.

As it can be more accurately seen in FIG. 3, the core 31 can in particular comprise two metallic blades 310, 311, substantially parallel and separated one from the other along the perimeter of the ring 31, for defining therebetween a zone adapted for fixing the collar to the prosthesis. These blades are connected one to the other at their free ends, 310 and 311 (FIG. 2). The nominal diameter of the collar is preferably equal, or slightly inferior, to the diameter of the duct 10, for naturally and very slightly squeezing it, and preventing the duct to inflate, despite the internal, radial thrust of the implant 1.

This opened annular frame is covered with a protecting layer made of a self-sealing material 33.

Thus, the core 31 is not aggressive for the patient body.

It is to be noted that instead of metal (which is radio-opaque), the core 31 could be made of a plastic material having a spring effect, such as vinyl polychloride (PVC) or polycarbonate. As metal, an inoxidable steel (Phynox, in particular, TM) or a memory shape alloy, such as Nitinol (TM) can be used.

The material of covering 33 can be a biocompatible silicone. On its external surface, the collar made of such a material further comprises a strap 35 lining the thus covered core. The strap 35 extends all along the perimeter of the covered collar and is continued beyond the perimeter of the core 31, at the place of extensions 350, 351, as shown in FIG. 2.

Preferably, the extensions 350 and 351 which are disposed on both sides of core 31 will have a full length at least substantially equal to the length of the core perimeter P. It is to be noted that this length P will typically be less than the external circumference of the duct to be treated, for preventing the core to be disposed all around.

The strap 35 can be made of cloth (such as Dacron, TM) or biocompatible felt, or very flexible plastic material, so that the strap can have the shape required by the practitioner to be dividable by surgical pliers, even if the cut must be operated in the patient body.

For a good sealing quality relative to various vessel diameters, the protecting self-obturing covering 33 preferably extends beyond the limits 312, 313 of the core 31, up to marks referenced 330 and 331 in FIG. 2, viz. along a portion of the length of the strap extensions 350, 351.

In FIG. 3, the complementary layer 52 is also lining the collar 29, at all. It is a layer having an hemostatic capacity, for example made of felt or foamed Teflon (TM), or a composite braiding. Such an hemostatic strip is often technically called as pledget and designed to reduce a bleeding when the strip is pressed to the leakage.

Of course, it will be understood that the hemostatic layer 52 will be disposed on the inner side (INT) of ring 29, to be directly pressed to the external wall 10a of vessel 10 (FIG. 6).

For introducing the (each) ring 29, a sheath 40, often called a trocar in the field of endoscopy/laparoscopy, can be used.

Moreover, this less invasive operating approach will be used for introducing, operating and fixing the (each) ring 29.

Thus, in FIG. 4, the trocar 40 encloses the ring 29 and coelioscopic pliers 54 the jaws 56 of which hold an end of the strap 35 for pulling inside the patient body the illustrated ring (see arrow 58) which then is in a substantially flat, deformed position, while having a split annular portion 31 completely opened and elastically stressed.

Since coelioscopy is a known operating approach, it will not be presently described. It is only to be noted that various transcutaneous, corporal operating approaches (including an opening of the vessel, or not) can be followed for introducing the ring(s) on the one side, and disposing a coelioscopic surgical tool to be used, such as for example second pliers referenced 60 in FIG. 5, on the other side.

In FIG. 5, the ring 29 is still in position around vessel 10 to be treated. Under the pulling action of plier 54, it has been removed from the trocar 40 (within the patient body) wherein second pliers (such as pliers 60) was waiting for disposing the ring as far as possible around the vessel (it is to be noted that passing the ring around the vessel can be delicate or impossible, in particular for the aorta, because tissues are attaching it to the vertebral column, presently referenced 44).

Nevertheless, where it is appropriate to dispose the ring 29 around the anatomic duct to be treated (or a supplementary organ), this ring can be used as a lace to make the surgeon action easier. Therefore, the latter will use in particular pliers 54, 60 (FIG. 5) or other coelioscopic tools, for operating the corresponding duct or organ, through the ring strands the flexibility of which makes the required mobility of the duct or the organ easier, possibly in connection with the relative stiffness of the frame 31.

As the ring has performed such function of moving means for the duct or the organ, the ring is disposed at the upper neck (or the lower neck) of vessel 10, within which the prosthesis is already disposed.

In FIG. 6, the collar and the prosthesis are already in position, the annular frame of the collar being closed itself around the external wall 10a of the vessel, further to releasing it of any restraint for opening imposed by pliers 54, 60.

According to an embodiment, the hemostatic layer 52 could be changed into treating the surface (in particular smearing) with a coagulating product, or a product which is dispersed, or embedded, in the covering 33 and/or strap 35.

Figure 7:
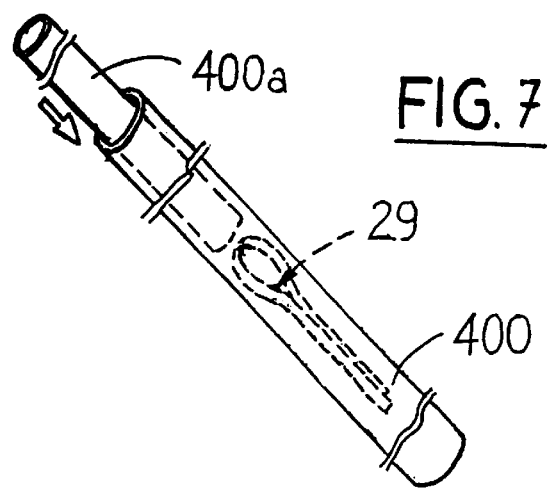
FIG. 7 shows how to introduce the ring of FIG. 2 by means of a catheter having a pusher.

It will be further noted that instead of disposing the ring 29 essentially flat, it could be decided to introduce it within a sheath 400 while pressing it on itself and pushing it with a flexible pusher 400a, as illustrated in FIG. 7.

As the ring is pushed out of sheath 400, it can be grasped by the surgeon pliers, within the patient body.

Figure 8:
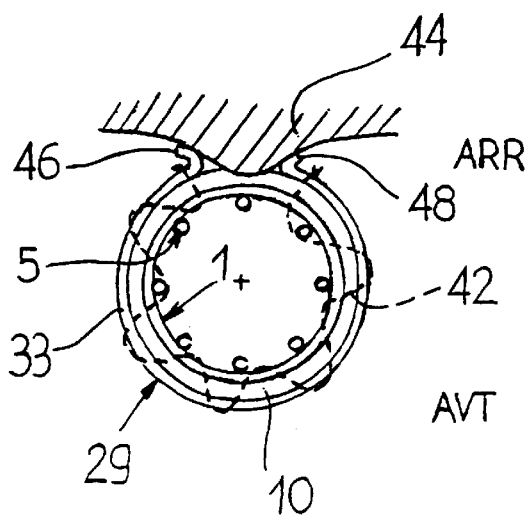
FIG. 8 shows a schematic section of a sealing ring disposed around an aorta which adheres to the corporal tissues, the ring being fixed to the internal aortic prosthesis.

If the operation is to be made around a human aorta backwardly connected (ARR) to corporal tissues 44, as illustrated in FIG. 8, the surgeon will engage the ring 29 forwardly (referenced AVI) while opening the split 37 thereof, in particular through pulling the strap portions 350, 351, and then releasing the strength until the ring closes up around the vessel.

The practitioner will then adapt the length of the strap by cutting the extensions thereof (cuts referenced 46 and 48). Preferably, the portion of the ring where the self-obturating, protecting cover 33 extends will be so cut, for improving the imperviousness thereof.

The practitioner will then fix the ring 29 and the internal prosthesis 1 together, through the intermediate vessel 10. In FIG. 8, a surgical suture 42 is diagrammatically illustrated for showing such a connection which passes several times through all the set comprising the ring/vessel/implant from outside the ring 29, while passing around one or more stent segments 5, if useful. (Preferably, the required needle will have a section less than the thread one, for improving the imperviousness).

Of course, more than one suture threads can be used and the way followed by thread 42 in FIG. 5 is only an illustration of a general principle for suturing, well known by the surgeons (vascular surgeons, in particular).

Laparoscopic trocar will be used for introducing the fixing means (suture threads together with operating pliers, rivets such as in FR 97 16625) and pliers will be used for intracorporally operating them.

The radio-opaque marking of leaves 310, 311, or any other metallic element added to the collar 29, shows the practitioner where the connection has to take place.

Figure 9:
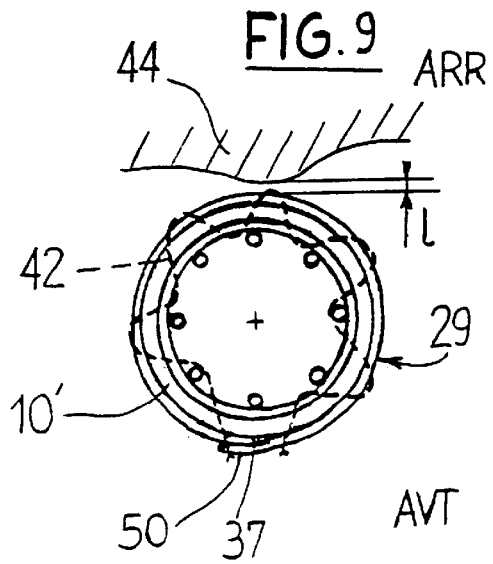
FIG. 9 is an embodiment wherein the duct is separated from the corporal tissues, while the ring is disposed all around said duct.

In FIG. 9, the duct (referenced 10') in which is received the aneurism prosthesis 1, is slightly separated from the corporal tissues 44 (distance 1). Then, it could be advantageous for the practitioner to dispose forward (AVT) the opened split 37 of the elastic ring 29, rather than backward (ARR) near the tissues 44.

Then the practitioner presses altogether, blood tightly, the duct and the prosthesis, from outside the ring, and thus outside the duct, for example one more time with a surgical suture thread 42, at least at the upper neck 23a, where most of the blood flow 25 enters.

As previously described, the ring 29 (and in particular the splitted ring 31 thereof) is used as an outer support, or strengthener, for the connection and the imperviousness.

Figure 10:
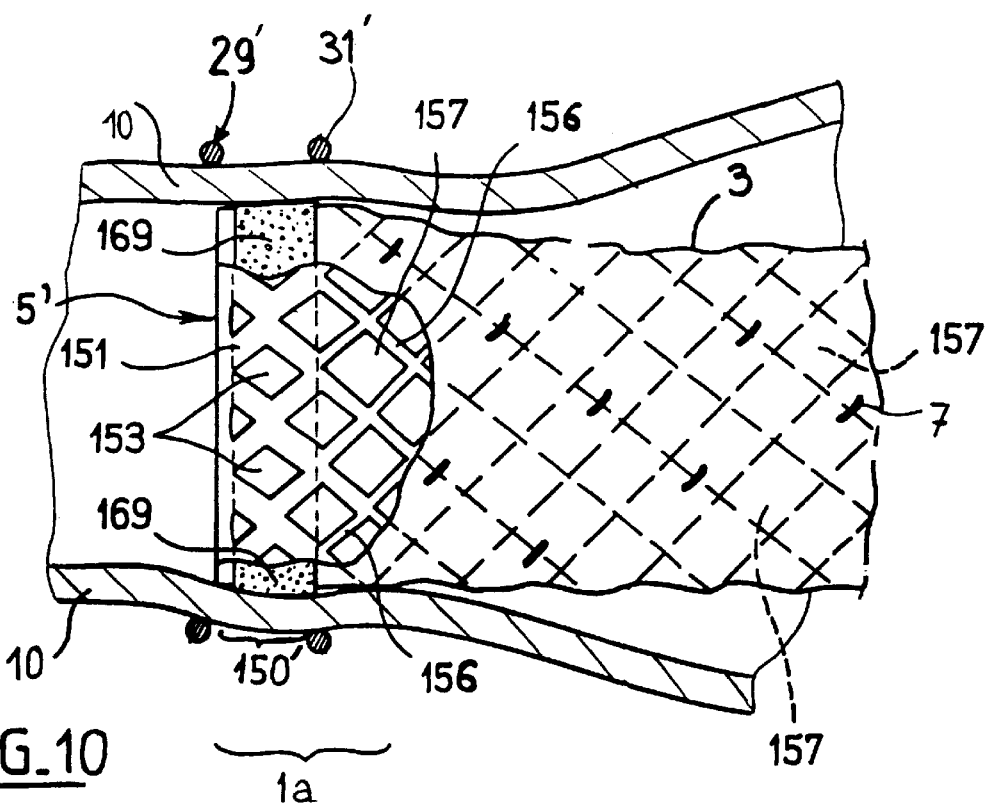
FIG. 10 shows, in a perspective view where the receiving duct is cut, an embodiment of the set comprising the ring and the prosthesis.

Moreover, the prosthesis can be associated to an internal strengthener 150' adapted to increase from the inside the pressure strength exerted by the prosthesis on the vessel wall, at the place of one and/or the other necks, as shown in FIG. 10, according to an embodiment. Therefore, the ring 150' is adapted to have its shape changed, preferably in a resilient manner.

This strengthener can be structurally independent from the prosthesis (referenced 150, FIG. 1), and will then preferably be implanted after the prosthesis. As an alternative, it can be directly integrated therein into one piece (FIGS. 10 and 11, references 150' and 150" respectively).

Wherever the strengthener is independent from the prosthesis, the frame thereof can substantially be the same as the one of the ring 31 (splitted ring).

Wherever the strengthener is integrated to the prosthesis, the frame of the latter can be modified so that the proximal portion thereof (or upstream portion) 1a and possibly the downstream portion, consist(s) of a strengthener 150' (FIG. 10). The metallic elements which presently define this frame have a larger section. It is zigzag thread(s), the diameter of their thread is larger. In FIG. 10, the example shows metallic bars 151 which are disposed on the terminal section 1a, and which limit the cells 153, are larger than the bars 156 pertaining to the remaining frame 5'. Thus, the cells 153 are smaller than the cells 157 which allow the radial expansion of the remaining frame to be obtained.

Figure 11:
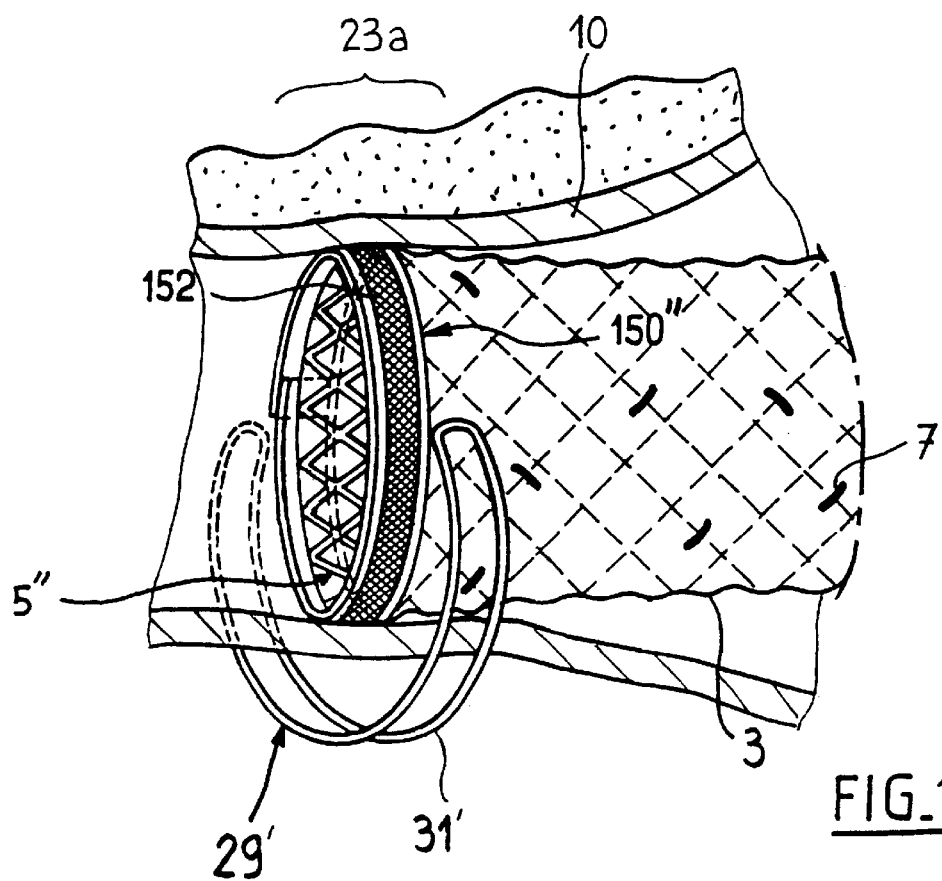
FIG. 11 is a further embodiment of the same set as illustrated in FIG. 10.

In FIG. 11, frame 5" is already internally disposed and is already defined, in the radially deployed state thereof, as a cylindrical tube having a (substantially) circular section, opened as a grid having diamond-shaped cells. The techniques known as laser piercing of a metallic tube having non-opened walls, can be used therefor. The strengthener 150" is now peripherically disposed outside the implant, to be directly pressed to the neck 23a. Small holes (not illustrated) can be provided for passing attaching ties through the strengthener, the stent and the sheath 3.

In particular for possibly preventing the implant to have anchoring hooks, the external surface 152 of strengthener 150" can be slightly abrasive or non-skid.

As it is an independent piece, the separating force of the frame will preferably be stronger than the one of a usual stent In the embodiment of FIGS. 10 and 11, it will be noted that the external ring 29' consists solely of a thread 31' which is folded for having two hoopings which are parallel and a separated from a constant distance substantially equal to the width of the strengthener. So, the latter is engaged in the unfolded position of the set between two hoopings and has thus no translation. Such a solution comprising hoopings can also be applied to a ring having a non-opened surface and, then, said hoopings inwardly project to reserve an annular zone adapted to receive said strengthener.

Further, it is possible to add a pad made of a biocompatible foam, between the prosthesis and the vessel wall, for preventing said wan to be damaged, on the one side, and improve the tight-impervious contact between the prosthesis and the vessel wall, while absorbing the imperfections of said wall, on the other side. The annular pad, diagrammatically represented in 169, in FIG. 10, will preferably cover the prosthesis, outwardly, before the implantation thereof, at the place of the proximal and/or distal portion thereof.

As an alternative embodiment it could be decided to adapt the 20 above-described set for implanting it is another anatomic duct, such as the gall bladder, see WO-A-97/09008 (dimensions, material, . . . , ref. P. 8 to 11).

What is claimed is:

1. A method for implanting a medical prosthesis into a duct of a living body, the method comprising:

provhiding at least one naturally curved strap comprising a rigid structure which is deformable between a first position in which it has an opened section ring shape showing a ring opening having a determined width and a second position in which said ring opening width is enlarged, disposing the medical prosthesis into the duct, said duct having a duct wall, introducing said at least one strap into the body, said at least one strap having in said body a second constrained position, allowing said at least one strap to deform from the second position toward the first position, while disposing said at least one strap around the duct wall, so that said at least one strap, which is externally facing the medical prosthesis, naturally closes up toward the duct, and, securing said at least one strap around the duct by using fastening means introduced into the body, said fastening means being distinct and separate from both the medical prosthesis and the strap, said step of securing comprising the steps of:

having the fastening means punctured through the strap and having said fastening means emerging out of it, and further having said fastening means penetrated through the duct wall.

2. The method according to claim 1, wherein the step of securing comprises the step of:

surgically suturing said at least one strap and the duct wall all together.

3. The method of claim 1, wherein the step of disposing the medical prosthesis further comprises the step of:

endoluminally inserting the medical prosthesis into the duct, the medical prosthesis having an axis and a length along said axis, so that the medical prosthesis is internally lining the duct along its length.

4. The method according to claim 1, wherein the step of securing said at least one strap around the duct comprises the step of engaging said fastening means through said strap, from outside the duct.

5. The method according to claim 1, wherein the step of disposing the medical prosthesis into the duct comprises the step of providing a medical prosthesis comprising a tubular sleeve.

6. The method according to claim 1, wherein the step of disposing the medical prosthesis into the duct comprises the steps of:

providing a medical prosthesis comprising a tubular sleeve made of cloth, and radially expanding the sleeve in the duct.

7. The method according to claim 1, wherein the step of disposing the medical prosthesis into the duct comprises the steps of:

providing a medical prosthesis comprising a tubular sleeve made of a synthetic, flexible, biocompatible material, and, radially expanding the sleeve in the duct.

8. The method according to claim 1, wherein the step of disposing the medical prosthesis into the duct comprises the steps of:

providing a medical prosthesis comprising a tubular sleeve adapted for canalizing blood there through, and an expandable stent structure, and, radially expanding the medical prosthesis in the duct.

\* \* \* \* \*